US007823722B2

(12) United States Patent
Bezou et al.

(10) Patent No.: US 7,823,722 B2
(45) Date of Patent: Nov. 2, 2010

(54) PACKED AND READY TO USE INTRALUMINAL CATHETER

(75) Inventors: Pascal Bezou, Authon du Perche (FR); Remi Collin, Saint Hilaire sur Eure (FR)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days.

(21) Appl. No.: 12/593,452

(22) PCT Filed: Mar. 26, 2008

(86) PCT No.: PCT/FR2008/050525

§ 371 (c)(1), (2), (4) Date: Sep. 28, 2009

(87) PCT Pub. No.: WO2008/129222

PCT Pub. Date: Oct. 30, 2008

(65) Prior Publication Data

US 2010/0116695 A1 May 13, 2010

(30) Foreign Application Priority Data

Mar. 27, 2007 (FR) .................................. 07 02234

(51) Int. Cl.
*A61B 19/02* (2006.01)

(52) U.S. Cl. ...................................... 206/210; 206/364

(58) Field of Classification Search ................. 206/207, 206/210, 363, 364, 365, 366, 438
See application file for complete search history.

(56) References Cited

U.S. PATENT DOCUMENTS 6,059,107 A 5/2000 Noested et al.
7,434,687 B2 * 10/2008 Itou et al. .................... 206/370
2005/0109648 A1 5/2005 Kerzman et al.
2005/0211590 A1 * 9/2005 McClure et al. ............. 206/438
2006/0196783 A1 9/2006 Bruun et al.
2008/0179208 A1 * 7/2008 Murray et al. .............. 206/364

FOREIGN PATENT DOCUMENTS

DE 10213411 A1 10/2003
FR 2896420 A1 7/2007
WO WO-99/30761 A1 6/1999
WO WO-03/064279 A1 8/2003

* cited by examiner

*Primary Examiner*—Jacob K Ackun, Jr.
(74) *Attorney, Agent, or Firm*—Fulbright & Jaworski LLP

(57) ABSTRACT

A packed intraluminal probe comprises a tube provided with a hydrophilic coating and having a proximal holding end connected to a nozzle. The nozzle has a canal communicating with the tube and an orifice. The probe is entirely arranged in a flexible, transparent and hermetic package. The probe comprises a removable stopper which closes the orifice. The package is fixed to the nozzle in a hermetic manner such that the nozzle defines two hermetic chambers which communicate only by means of the lumen of the tube and the canal in the nozzle. A first chamber contains a wetting fluid for the coating of the tube, but a second chamber does not contain any wetting fluid.

9 Claims, 1 Drawing Sheet

18 16 30 14 15 12 20 26 22 30 32 28 34 24 10

PACKED AND READY TO USE INTRALUMINAL CATHETER

RELATED APPLICATIONS

This application is a §371 application from PCT/FR2008/050525 filed Mar. 26, 2008 which claims priority from French Patent Application No. 07 02234 filed Mar. 27, 2007, each of which is herein incorporated by reference in its entirety.

TECHNICAL FIELD OF THE INVENTION

The present invention refers to an intraluminal probe packed in a ready-to-use state. Such probes are intended to be introduced into body ducts, for example into urethra.

BACKGROUND OF THE INVENTION

Intraluminal probes are used in a ready-to-use form or must be wetted before use. As this probe type has the disadvantage of making the handling by the user more complicated, the objective is to realize ready-to-use probes.

Thus, ready-to-use intraluminal probes are arranged in a hermetic package which contains a wetting fluid, which causes a swelling of the hydrophilic coating of the probe which has thus a high slipping condition. Despite of the attempt of retaining the wetting fluid on the probe tube side, for example by means of absorbent pads or by forming fluid pockets, some wetting fluid happens to reach the probe nozzle which must be held in the hand, and makes it slippery.

In the case of the probes described in the document EP-935 478, the wetting fluid is always present on the probe nozzle which must be held in the hand, and which is thus slippery.

Another disadvantage of the well-known systems is that, when the intraluminal probe is packed between two welded sheets of plastic material, the opening is realized by tearing the package from a tearing incision. When the package is thereby open, the nozzle must be held with a part of the package, so that the wetting fluid can flow to the orifice side of the nozzle which can be wetted before being hold.

OBJECT AND SUMMARY OF THE INVENTION

An object of the invention is to solve the problem of handling these intraluminal probes. More precisely, an object of the invention is, on one hand, to prevent any wetting fluid from flowing to the nozzle side opposed to the probe tube and, on the other hand, to make the handling easier after the opening by tearing the package from the initial incision.

According to the invention, the above-mentioned problem is solved because the hermetic package is fixed around the nozzle in a hermetic manner in order that the nozzle defines on both sides two chambers separated in a hermetic manner, and because the nozzle is closed by a stopper.

More precisely, the invention refers to an intraluminal probe packed in a ready-to-use state, of the type which comprises a tube provided with a hydrophilic coating and having a distal insertion end and a proximal holding end connected to a nozzle, which has a canal communicating on one side with the tube and opening on the other side through an orifice, the probe being entirely arranged in a hermetic package; according to the invention, the packed probe comprises a removable stopper which closes the nozzle orifice in a hermetic manner, the package is fixed to the nozzle in a hermetic manner in order that said nozzle defines, in the package, two hermetic chambers which communicate only by means of the tube lumen and the nozzle canal, a first chamber in which the tube is arranged contains a wetting fluid for the hydrophilic coating of the tube in order to provide it with a high slipping condition, and the second chamber in which the orifice opens virtually contains no wetting fluid.

Preferably, the package is formed of two sheets of plastic material fixed around the nozzle in a hermetic manner.

Preferably, the fixation is realized by a welding or bonding process.

Preferably, both package sheets of plastic material have at least one transversal tearing incision on both sides of the nozzle.

Preferably, both package sheets of plastic material have two tearing incisions on the tube side: one incision near the nozzle and the other a little further from it.

Preferably, the package sheets have low vapor permeability.

Preferably, the package sheets are formed of a polymer oriented such that the stretching direction of the polymer is transversal to the tube direction.

Preferably, the wetting fluid is a hydrous solution.

Preferably, the hydrophilic tube coating swells in the presence of water.

Thus, one advantage of the invention is that the probe side opposed to the tube (nozzle) is always protected against the presence of wetting fluid, with the result that the convenient hold of the probe and its connection to a reception unit is always easy.

BRIEF DESCRIPTION OF THE DRAWINGS

Other characteristics and advantages of the invention will better understood from the reading of the following description of embodiments, while referring to the annexed figures in which.

DETAILED DESCRIPTION OF THE EMBODIMENTS

Figure 1:
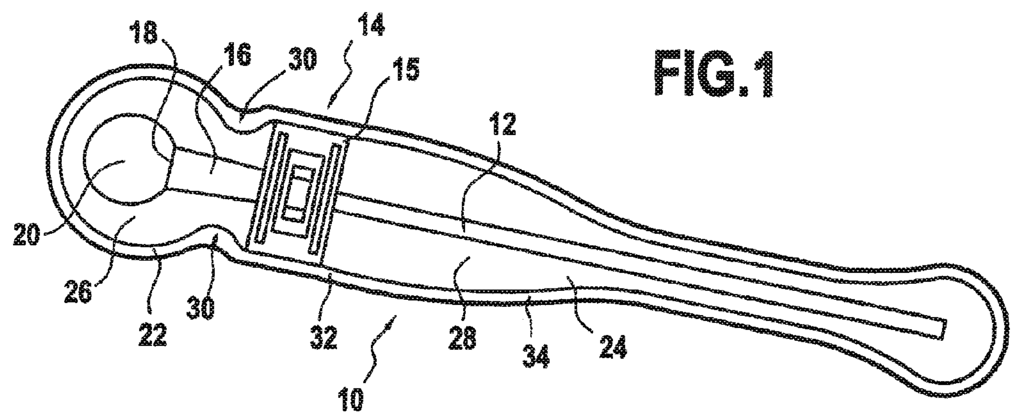
FIG. 1 is a top view of an example of an intraluminal probe packed according to the invention.

FIG. 1 represents an intraluminal probe packed according to the invention. This probe 10 comprises a tube 12, the external surface of which has a hydrophilic coating with a slipping condition when the coating is wet, a nozzle 14 composed of a base 15 and a duct portion 16 which ends through an orifice on the side opposed to the tube 12.

Figure 2:
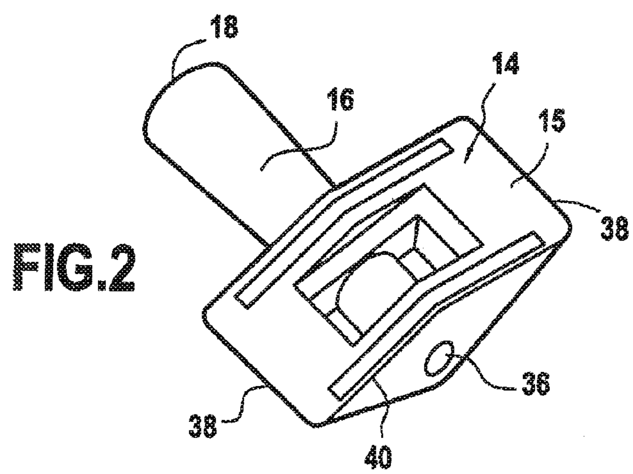
FIG. 2 is a perspective view of an example of a nozzle according to the invention.

In FIG. 2, it must be noted that the orifice 18 forms the open end of a canal which extends through the nozzle 14 up to an orifice 38 communicating with the lumen of the probe tube 12.

In FIG. 1, the reference 20 indicates a removable stopper placed on the orifice 18 and closing it in a hermetic manner.

According to the invention, both sheets of the package 22 form two chambers separated in a hermetic manner: a first chamber 24 in which the tube 12 is arranged and a second chamber 26 in which the duct portion 16 and the stopper 20 are arranged. The tightness between both chambers is realized by welding or bonding both sheets to the body of the nozzle 14 and one on the other.

As it is indicated in FIG. 2, the body of the nozzle 14 has a diamond-shaped section ending with two thin edges 38 and forming, between both edges 38, a continuous surface 40 which can be soldered or bonded to one package sheet. In case of welding, the package sheet of transparent plastic material and the plastic material of the nozzle 14 are preferably of the same chemical nature, for example polyethylene.

The package of the intraluminal probe according to the invention contains, in the chamber 24 in which the tube 12 is arranged, a wetting fluid providing the tube 12 with a high slipping condition. The fluid is advantageously a hydrous solution, of a type well-known in the art, the composition of which depends on the exact nature of the hydrophilic coating of the tube 12. Thus, although the package sheets are fixed to the nozzle 14 in a hermetic manner, both chambers 24, 26 communicate with the orifice 18 via the interior part of the tube 12 and the canal of the nozzle 14. A stopper 20 is placed on the orifice 18, by closing it in a hermetic manner, in order that the fluid in the chamber 24 cannot enter the chamber 26.

In FIG. 1, the references 30, 32 and 34 indicate tearing incisions enabling to tear the package in a direction transversal to the tube 12.

Figure 3:
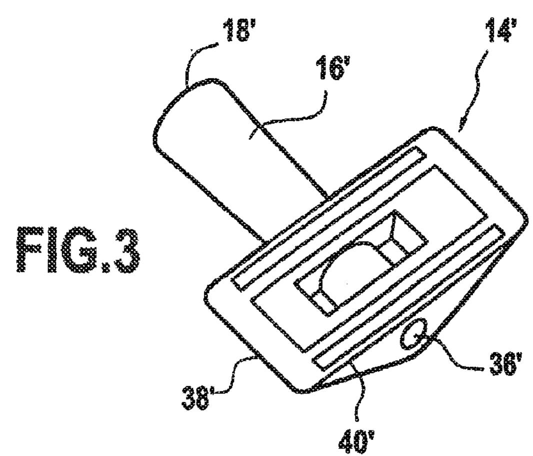
FIG. 3 is a perspective view of a nozzle variant.

FIG. 3 represents a nozzle variant, with a flat side sometimes useful for the handling. In the variant in FIG. 3, the references followed by the sign ' indicate elements similar to those in FIG. 2. This variant will not be thus described in more detail.

In FIG. 1, it can be seen that the probe can be freed in use by removing the package part between the tearing incision 32 and the end near the insertion end for the tube 12.

According to the invention, it is however advantageous to separate the package at the tearing incision 34 first, so that the tube insertion end is freed. Then, the remaining part of the package is torn from the tearing incision 32. The package portion between the tearing incisions 32 and 34 forms then a kind of sleeve which can be nipped between two fingers to make the probe handling easier. Thus, the user normally holds the base 15 of the nozzle 14 with the left hand and the sleeve between the tearing incisions 32 and 34 with the right hand. When displacing this sleeve to the insertion end, the user holds the end of the tube to be inserted with a good precision, and without touching it with the fingers ("no touch" technique). During the tube insertion by applying a force along it, the sheath is guided with the right hand to the base as far as an appropriate insertion depth.

At this moment, or before the preceding operation, the package part placed on the other side of the nozzle 14 can be torn at the tearing incision 30. The user, who still holds the base with the left hand, can then remove the stopper 20 and connect the nozzle to a device for receiving a fluid evacuated by the probe.

It is advantageous to remove the package part placed on the other side of the nozzle 14 and the stopper in one operation.

In this last operation, the wetting fluid around the tube 12 is retained by the package part between the base and the incision 32, so that the fluid can soil neither the tube portion 16 nor the stopper 20, and the handling is very safe and convenient.

The fabrication of probes according to the invention does not present any technical difficulties, as it is simple to weld the package sheets onto the nozzle during the welding operation for the sheets one on the other, when the package is being hermetically closed. In an embodiment, this welding operation is realized by welding both sheets onto the nozzle first, then by welding the sheet edges, except the nearest end relative to the insertion end of the tube 12. The wetting fluid intended to provide the hydrophilic coating of the tube 12 with slipping properties is indeed introduced once the package is closed, except at that nearest end, and this end is welded only at this moment.

The sterilization can be realized with conventional processes, without any modification.

Although it has been described a package formed of two welded sheets, it is evident that it can be formed of one folded sheet welded on itself.

The invention claimed is:

1. An intraluminal probe packed in a ready-to-use state and entirely arranged in a hermetic package, comprising a tube provided with a hydrophilic coating and having a distal insertion end and a proximal holding end;

a nozzle connected to the proximal holding end of the tube, and comprising a canal communicating on one side with the tube and opening on the other side through an orifice; and a removable stopper closing the orifice of the nozzle in a hermetic manner; and wherein the package is fixed to the nozzle in a hermetic manner such that the nozzle defines two hermetic chambers in the package, a first chamber and a second chamber communicate only by means of a lumen of the tube and the canal in the nozzle;

wherein the tube is arranged in the first chamber containing a wetting fluid for the hydrophilic coating of the tube, thereby providing a slippery tube; and wherein the orifice of the nozzle opens in a second chamber containing virtually no wetting fluid.

2. The intraluminal probe of claim 1, wherein the package is formed of two package sheets of plastic material fixed around the nozzle in a hermetic manner.

3. The intraluminal probe of claim 2, wherein the package is fixed to the nozzle by a welding or bonding process.

4. The intraluminal probe of claim 2, wherein the two package sheets have at least one transversal tearing incision on both sides of the nozzle.

5. The intraluminal probe of claim 4, wherein the two package sheets have two tearing incisions on a side of the tube, one tearing incision near the nozzle and another tearing incision further from the nozzle.

6. The intraluminal probe of claim 2, wherein the two package sheets have low vapor permeability.

7. The intraluminal probe of claim 2, wherein the two package sheets are formed of a polymer oriented such that a stretching direction of the polymer is transversal to a longitudinal direction of the tube.

8. The intraluminal probe of claim 1, wherein the wetting fluid is a hydrous solution.

9. The intraluminal probe of claim 1, wherein the hydrophilic coating of the tube swells in the presence of water.

* * * * *